United States Patent [19]

Schmidt et al.

[11] 4,210,648

[45] Jul. 1, 1980

[54] 11-AMINOACYL-5,11-DIHYDRO-6H-PYRIDO(2,3-B)(1,4)BENZODIAZEPIN-6-ONES AND SALTS THEREOF

[75] Inventors: Günther Schmidt; Mátyás Leitold, both of Biberach an der Riss, Fed. Rep. of Germany

[73] Assignee: Boehringer Ingelheim GmbH, Ingelheim am Rhein, Fed. Rep. of Germany

[21] Appl. No.: 907,823

[22] Filed: May 19, 1978

[30] Foreign Application Priority Data

May 31, 1977 [DE] Fed. Rep. of Germany ....... 2724478

[51] Int. Cl.$^2$ ............................................. A61K 31/55
[52] U.S. Cl. ............................ 424/256; 260/239.3 T; 424/246; 424/248.54; 424/251; 424/263; C07D/401/14
[58] Field of Search ............... 260/239.3 T; 424/263, 424/246, 248.54, 251, 256

[56] References Cited

U.S. PATENT DOCUMENTS

| | | | |
|---|---|---|---|
| 3,660,380 | 5/1972 | Schmidt et al. | 260/239.3 T |
| 3,691,152 | 9/1972 | Schmidt et al. | 260/239.3 T |

Primary Examiner—John M. Ford
Assistant Examiner—Robert T. Bond
Attorney, Agent, or Firm—Hammond & Littell, Weissenberger & Muserlian

[57] ABSTRACT

Compounds of the formula

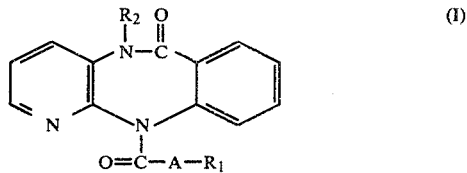

wherein

A is alkylene of 1 to 5 carbon atoms;

$R_1$ is amino, tert.butylamino, N-cyclohexyl-N-methyl-amino, dibenzylamino, benzylamino, trimethoxybenzyl-amino, 1-ethyl-2-pyrrolidinylmethylamino, 1-ethyl-3-piperidinyl-amino, 9-methyl-3,9-diazabicyclo[3.3.1]nonan-3-yl, 1,2,5,6-tetrahydro-1-pyridyl, 4-benzyl-piperidino, 1,2,3,6,7,8,9,9a-octahydro-4H-pyrazino[1,2-a]-pyrimidine-1(or-8)yl, 3- or 4-hydroxypiperidino, 3-or 4-methoxypiperidino, 1,2,3,4-tetrahydro-2-isoquinolyl, 3-azaspiro[5.5]undecan-3-yl, 4-oxo-piperidino or the ethyleneketal thereof, hexahydro-3-methyl-1-pyrimidinyl, thiomorpholino, 1-oxido-thiomorpholino, hexahydro-4-methyl-1H-1,4-diazepin-1-yl, 2,6-dimethyl-morpholino,1,4-diazabicyclo [4.3.0]nonan-4-yl, 1,2,5,6-tetrahydropyrid-1-yl, (1-methylpyrrolindin-2-yl)-ethylamino, (1-methylpyrrolidin-2-yl)-methylamino, (1-n-propylpyrrolidin-2-yl)-methylamino, (1-allyl-pyrrolidin-2-yl)-methylamino, (1-n-butyl-pyrrolidin-2-yl)-methylamino, (1-benzyl-pyrrolidin-2-yl)-methylamino, (furan-2-yl)-methylamino, (tetrahydrofuran-2-yl)-methylamino, N-[(1-ethyl-pyrrolidin-2-yl)-methyl]-methylamino, (1-ethyl-pyrrolidin-3-yl)-methylamino or (1-allylpyrrolidin-3-yl)-methylamino; or, when A is alkylene of 2 to 5 carbon atoms, also dimethylamino, diethylamino, dipropylamino, diisopropylamino, di-n-butylamino, diisobutylamino, pyrrolidino, piperidino, methyl-piperidino, ethyl-piperidino or morpholino; and $R_2$ is hydrogen, methyl or ethyl;

and non-toxic, pharmacologically acceptable acid addition salts thereof. The compounds as well as the salts are useful as anti-ulcerogenics and secretion inhibitors.

5 Claims, No Drawings

11-AMINOACYL-5,11-DIHYDRO-6H-PYRIDO(2,3-B) (1,4)BENZODIAZEPIN-6-ONES AND SALTS THEREOF

This invention relates to novel 11-aminoacyl-5,11-dihydro-6H-pyrido[2,3-b][1,4]benzodiazepin-6-ones and non-toxic acid addition salts thereof, as well as to a method of preparing these compounds.

More particularly, the present invention relates to a novel class of compounds represented by the formula

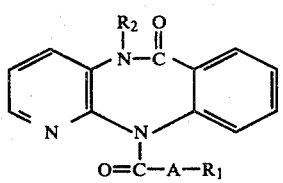

wherein
A is alkylene of 1 to 5 carbon atoms;
$R_1$ is amino, tert.butylamino, N-cyclohexyl-N-methyl-amino, dibenzylamino, benzylamino, trimethoxybenzyl-amino, 1-ethyl-2-pyrrolidinylmethylamino, 1-ethyl-3-piperidinyl-amino, 9-methyl-3,9-diazabicyclo-[3.3.1]nonan-3-yl,1,2,5,6-tetrahydro-1-pyridyl, 4-benzyl-piperidino, 1,2,3,6,7,8,9,9a-octahydro-4H-pyrazino [1,2-a]-pyrimidine-1(or-8)yl, 3- or 4-hydroxypiperidino, 3-or4-methoxypiperidino, 1,2,3,4-tetrahydro-2-isoquinolyl, 3-azaspiro [5.5]undecan-3-yl, 4-oxopiperidino or the ethyleneketal thereof, hexahydro-3-methyl-1-pyrimi-dinyl, thiomorpholino, 1-oxido-thiomorpholino, hexahydro-4-methyl-1H-1,4-diazepiin-1-yl, 2,6-diamethyl-morpholino,1,4-diazabicyclo [4.3.0]nonan-4-yl, 1,2,5,6-tetrahydro-pyrid-1-yl, (1methylpyrrolidin-2yl)-ethylamino, (1-methylpyrrolidin-2-yl)-methylamino, (1-n-propylpyrrolidin-2-yl)-methylamino, (1-allyl-pyrrolidin-2-yl)-methylamino, (1-n-butyl-pyrrolidin-2yl)-methylamino, (1-benzyl-pyrrolidin-2-yl)-methylamino, (furan-2yl)-methylamino, (tetrahydrofuran-2-yl)-methylamino, N-[(1-ethyl-pyrrolidin-2-yl)-methyl]methylamino, (1-ethyl-pyrrolidin-3-yl)-methylamino or (1-allyl-pyrrolidin-3-yl)-methylamino or, when A is alkylene of 2 to 5 carbon atoms, also dimethylamino, diethylamino, dipropylamino, diisopropylamino, di-n-butylamino, diisobutylamino, pyrrolidino, piperidino, methylpiperidino, ethyl-piperidino or morpholino; and
$R_2$ is hydrogen, methyl or ethyl, and non-toxic, pharmacologically acceptable acid addition salts thereof.

The compounds embraced by formula I may be prepared by reacting an 11-haloacyl-5,11-dihydro-6H-pyrido[2,3-b][1,4]benzodiazepin-6-one of the formula

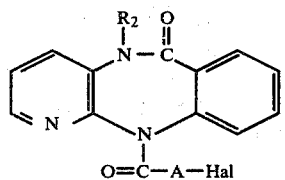

wherein
A and $R_2$ have the same meanings as in formula I, and Hal is halogen,
with an amine of the formula $$R_1-H \quad \text{(III)}$$

wherein $R_1$ has the same meanings as in formula I.

The reaction is advantageously carried out in an inert solvent, optionally in the presence of an acid-binding agent, and at elevated temperatures, preferably at the boiling point of the solvent which is used. Preferred solvents are alcohols, such as ethanol, n-propanol or isopropanol; ketones, such as acetone; ethers, such as dioxane or tetrahydrofuran; or aromatic hydrocarbons, such as benzene or toluene. It is advantageous to provide the amine of the formula III in sufficient excess to bind the liberated hydrogen halide; however, other hydrogen halide-binding agents, as for example alkali metal carbonates, alkali metal bicarbonates or tertiary organic amines, such as triethylamine, pyridine or dimethylaniline, may be added to the reaction mixture.

The reaction may proceed by splitting off hydrogen halide and forming as an intermediate a compound corresponding to formula II, but where the -A-Hal moiety is replaced by an alkenylene group; the amine of the formula III then attaches itself to this alkenylene group.

Accordingly, the compounds of the formula I can also be prepared by splitting off hydrogen halide from a compound of the formula II, dissolved in an inert solvent, by refluxing in the presence of a hydrogen halide-binding agent. The thus obtained compound of the formula II, wherein instead of a group —A—Hal there is an alkenylene group, is isolated and this intermediate is subsequently reacted in a suitable solvent with an amine of the formula III at temperatures up to the boiling point of the reaction mixture.

For the first reaction step, i.e. splitting off hydrogen halide, preferably high-boiling-point ethers like dioxane or tetrahydrofuran, or aromatic hydrocarbons, like benzene or toluene, may serve as solvents; suitable hydrogen halide-binding agents are, for example, alkali metal carbonates, alkali metal bicarbonates or tertiary organic amines, like triethylamine, pyridine or dimethylaniline. The reaction of the thus obtained intermediate with an amine of the formula III is carried out in a solvent, for example an alcohol like ethanol, n-propanol, isopropanol, or in a ketone like acetone, or in an ether like dioxane or tetrahydrofuran, or in an aromatic hydrocarbon like benzene or toluene.

The preparation of a compound of the formula I wherein $R_1$ amino ($-NH_2$) is in principle possible according to the above described process by reaction with ammonia under pressure in a closed vessel. It is, however, more advantageous for further processing of the reaction mixture and for obtaining sufficient yields to react a compound of the general formula II first with benzylamine or a ring-substituted derivative of benzylamine and to convert the thus obtained benzylamino compound according to known methods, for example by catalytic hydrogenation, into a compound of the formula I wherein $R_1$ is amino.

The starting compounds of the formula II can be prepared by reacting a 5,11-dihydro-6H-pyrido [2,3-b] [1,4]-benzodiazepin-6-one of the formula

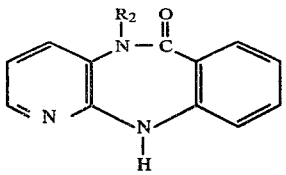

wherein R$_2$ has the same meanings as in formula I, with a haloacyl halide of the formula

wherein A has the same meanings as in formula I, and Hal and Hal' are each chlorine, bromine or iodine.

The reaction is preferably carried out in an inert solvent in the presence of a hydrogen halide-binding agent at elevated temperatures, preferably at the boiling point of the solvent which is used. Suitable solvents are aromatic hydrocarbons, such as benzene, toluene or xylene; or ethers, such as diethylether, dipropyl-ether or preferably cyclic ethers, like dioxane. Suitable hydrogen halide-binding agents are tertiary organic bases such as triethylamine, N,N-dimethylaniline or pyridine, or also inorganic bases, like alkali metal carbonates or alkali metal bicarbonates. The processing of the reaction mixture is carried out in the usual way; the yields amount up to 90% of theory. The formed haloacyl compounds of the formula II are mostly well crystallizable substances which can be used as such, without further purification, for the preparation of the compounds of the formula I.

For instance, the following compounds of the formula II were obtained by reacting the corresponding compound of the formula IV (a) with 2-chloropropionyl chloride in dioxane as solvent:
11-(2-chloropropionyl)-5,11-dihydro-6H-pyrido[2,3-b][1,4]-benzodiazepin-6-one
M.p.: 215°–218° C. (from ethanol)
and
11-(2-chloropropionyl)-5-methyl-5,11-dihydro-6H-pyrido [2,3-b]-[1,4]benzodiazepin-6-one
M.p.: 210°–212° C. (from acetonitrile),
(b) with 3-chloropropionyl chloride in dioxane as solvent:
11-(3-chloropropionyl)-5,11-dihydro-6H-pyrido[2,3-b][1,4]-benzodiazepin-6-one
M.p.: 216°–218° C. (decomp.),
(c) with 4-chlorobutyryl chloride in xylene as solvent:
11-(4-chlorobutyryl)-5,11-dihydro-6H-pyrido[2,3-b][1,4]benzodiazepin-6-one
M.p.: 205°–207° C. (from ethyl acetate),
(d) with 5-chlorovaleryl chloride in xylene:
11-(5-chlorovaleryl)-5,11-dihydro-6H-pyrido[2,3-b][1,4]benzodiazepin-6-one
M.p.: 170°–172° C. (from n-propanol),
(e) with 6-chlorocaproyl chloride in xylene:
11-(6-chlorocaproyl)-5,11-dihydro-6H-pyrido[2,3-b][1,4]benzodiazepin-6-one
M.p.: 128°–130° C. (decomp.), From the thus obtained 11-haloacyl-5,11-dihydro-6H-pyrido-[2,3-b][1,4]benzodiazepin-6-ones one can easily, as described above, obtain the intermediates having in 11-position an alkenylacyl group, which can subsequently be reacted with an amine of the formula III. Thus, for example, from 11-(3-chloropropionyl)-5,11-dihydro-6H-pyrido[2,3-b][1,4]benzodiazepin-6-one in dioxane as solvent, 11-(acryloyl)-5,11-dihydro-6H-pyrido[2,3-b][1,4]benzodiazepine-6-one, M.p.: 235° C. (decomp.) (from acetonitrile), was obtained with high yield after 1 hour of refluxing in the presence of an excess of triethylamine (see German Pat. No. 1,936,670).

The compounds of the formula IV are known from literature (see German Pat. Nos. 1,179,943 and 1,204,680).

The compounds of the formula I are organic bases and therefore form acid addition salts with inorganic or organic acids. Examples of non-toxic, pharmacologically acceptable acid addition salts are those formed with hydrochloric acid, hydrobromic acid, sulfuric acid, phosphoric acid, acetic acid, fumaric acid, citric acid, maleic acid, succinic acid, oxalic acid, 8-chlorotheophylline or the like.

The following examples illustrate the present invention and will enable others skilled in the art to understand it more completely. It should be understood, however, that the invention is not limited solely to the particular examples given below.

EXAMPLE 1

11-{[(1-Ethyl-2-pyrrolidinyl)methylamino]acetyl}-5,11-dihydro-5-methyl-6H-pyrido[2,3-b][1,4]benzodiazepin-6-one 9.0 gm of 11-chloroacetyl-5,11-dihydro-5-methyl-6H-pyrido[2,3-b]-[1,4]benzodiazepin-6-one, 3.5 gm of sodium carbonate and 4 gm of 1-ethyl-2-amino-methyl-pyrrolidine were refluxed in 100 ml of ethanol for 1.5 hours. Then the hot mixture was suction-filtered, the filtrate was evaporated in vacuo to dryness, and the residue was recrystallized from acetonitrile and subsequently from ethyl acetate, yielding 48% of theory of the compound of the formula

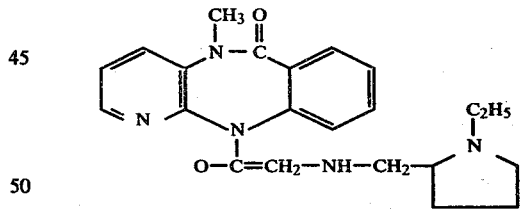

which had a melting point of 169°–171° C. Its dihydrochloride had a melting point of 196°–198° C. (from ethanol).

EXAMPLE 2

5,11-Dihydro-11-[(4-methoxypiperidino)acetyl]-6H-pyrido [2,3-b]-[1,4]benzodiazepin-6-one 5.8 gm of 11-chloroacetyl-5,11-dihydro-6H-pyrido [2,3-b][1,4]benzodiazepin-6-one and 15 ml of 4-methoxypiperidine were refluxed in 200 ml of benzene for 15 hours. Then the hot mixture was suction-filtered, the solvent was distilled off, and the residue was recrystallized from isopropanol.

M.p.: 219°–220° C.
Yield: 55% of theory.

EXAMPLE 3

11-(Dibenzylamino-acetyl)-5,11-dihydro-6H-pyrido [2,3-b][1,4]benzodiazepin-6-one 6 gm of 11-chloroacetyl-5,11-dihydro-6H-pyrido [2,3-b][1,4]benzodiazepin-6-one, 4.2 gm of dibenzylamine and 2.1 gm of triethylamine were refluxed in 100 ml of absolute dioxane for 15 hours. After cooling, the formed triethylamine hydrochloride was separated, and the filtrate was evaporated in vacuo to dryness. The residue was then recrystallized twice from ethanol.

M.p.: 187°–189° C.

Yield: 60% of theory.

EXAMPLE 4

5,11-Dihydro-11-[3-(2-methylpiperidino)propionyl]-6H-pyrido-[2,3-b][1,4]benzodiazepin-6-one 16 gm of 11-(3-chloropropionyl)-5,11-dihydro-6H-pyrido [2,3-b]-[1,4]benzodiazepin-6-one were, after addition of 20 ml of 2-methylpiperidine, refluxed for 1 hour in 200 ml of isopropanol, and the reaction mixture was then evaporated in vacuo to dryness. The residue was admixed with water, the mixture was made alkaline by addition of ammonia and extracted with chloroform. The evaporation residue of the chloroform extract was purified on a silica gel column. The eluate was then evaporated in vacuo to dryness, and the residue was recrystallized from isopropanol.

M.p.: 197°–199° C. (under decomposition).

Yield: 65% of theory.

EXAMPLE 5

5,11-Dihydro-11-(3-piperidinopropionyl)-6H-pyrido [2,3-b][1,4]-benzodiazepin-6-one 4.9 gm of 11-acryloyl-5,11-dihydro-6H-pyrido[2,3-b][1,4]benzodiazepin-6-one were after addition of 15 ml of piperidine, refluxed in 150 ml of dioxane for 2 hours. The solvent and excess amine were then distilled off in vacuo, and the residue was recrystallized from n-propanol.

M.p.: 230° C. (decomposition).

Yield: 72% of theory.

EXAMPLE 6

11-[3-(Benzylamino)propionyl]-5,11-dihydro-6H-pyrido[2,3-b]-[1,4]benzodiazepin-6-one 6.0 gm of 11-(3-chloropropionyl)-5,11-dihydro-6H-pyrido [2,3-b]-[1,4]benzodiazepin-6-one, 2.3 gm of sodium carbonate and 4.4 gm of benzylamine were refluxed in 80 ml of ethanol for 4 hours. Then the hot mixture was suction-filtered, the alcohol was distilled off, and the residue was purified on a silica gel column. The evaporation residue of the eluate was recrystallized twice from n-propanol.

M.p.: 155°–158° C.

Yield: 41% of theory.

EXAMPLE 7

11-(3-Aminopropionyl)-5,11-dihydro-6H-pyrido[2,3-b][1,4]benzodiazepin-6-one 16.4 gm of 11-[3-(benzylamino)propionyl]-5,11-dihydro-6H-pyrido-[2,3-b][1,4]benzodiazepin-6-one (prepared according to Example 6), together with 3 g of palladium-on-charcoal, were hydrogenated in 300 ml of absolute ethanol for 7 hours at 70° C. and 5 atm. Then the catalyst was filtered off, the alcohol was distilled off, and the residue was purified on a column. After evaporation of the eluate, the residue was recrystallized from ethanol.

M.p.: 198°–200° C.

Yield: 37% of theory.

EXAMPLE 8

11-[4-(Diethylamino)butyryl]-5,11-dihydro-5-methyl-6H-pyrido-[2,3-b][1,4]benzodiazepin-6-one hydrochloride 4.3 gm of 11-(4-chlorobutyryl)-5,11-dihydro-5-methyl-6H-pyrido-[2,3-b][1,4]benzodiazepin-6-one and 1.9 gm of diethylamine were allowed to stand in 70 ml of dimethylformamide for 3 weeks at room temperature. Then the reaction mixture was evaporated in vacuo to dryness, and the residue was recrystallized from isopropanol. The hydrochloride, M.p.: 233°–235° C., was obtained.

Yield: 54% of theory.

EXAMPLE 9

5,11-Dihydro-11-(4-pyrrolidino-butyryl)-6H-pyrido[2,3-b][1,4]-benzodiazepin-6-one 5.5 gm of 11-(4-chlorobutyryl)-5,11-dihydro-6H-pyrido [2,3-b][1,4]-benzodiazepin-6-one, 1.4 gm of pyrrolidine and 2.1 gm of sodium carbonate were refluxed in a mixture of 80 ml of absolute ethanol and 20 ml of absolute dioxane for 10 hours. Then the hot mixture was suction-filtered, the filtrate was evaporated in vacuo to dryness, and the residue was purified on a silica gel column. The eluate was evaporated in vacuo to dryness, and the residue was recrystallized from acetonitrile.

M.p.: 163°–165° C.

Yield: 55% of theory.

EXAMPLE 10

11-[(1-Ethyl-3-piperidyl)aminoacetyl]-5,11-dihydro-6H-pyrido[2,3-b][1,4]benzodiazepin-6-one 7.2 gm of 11-chloroacetyl-5,11-dihydro-6H-pyrido [2,3-b][1,4]benzodiazepin-6-one, 2.8 gm of sodium carbonate and 3.8 gm of 1-ethyl-3-amino-piperidine were refluxed in 100 ml of ethanol for 5 hours. Then the hot mixture was suction-filtered, the filtrate was evaporated in vacuo to dryness, and the residue was purified on a silica gel column. The evaporation residue of the eluate was recrystallized from ethyl acetate.

M.p.: 147°–148° C.

Yield: 58% of theory.

EXAMPLE 11

5,11-Dihydro-11-[(hexahydro-4-methyl-1H-1,4-diazepin-1-yl)acetyl]-6H-pyrido[2,3-b][1,4]benzodiazepin-6-one dihydrochloride 8.6 gm of 11-chloroacetyl-5,11-dihydro-6H-pyrido[2,3-b][1,4]benzodiazepin-6-one, 3.5 gm of sodium carbonate and 4.5 gm of hexahydro-1-methyl-1H-1, 4-diazepine were refluxed in 100 ml of ethanol for 2.5 hours. Then the hot mixture was suction-filtered, the alcohol was distilled off, and the residue was triturated with dioxane. The precipitated crystals were dissolved in ethanol and converted into the dihydrochloride by addition of concentrated hydrochloric acid. After recrystallization from 94% ethanol:

M.p.: 241°–243° C (decomposition).

Yield: 47% of theory.

EXAMPLE 12

5,11-Dihydro-11-(5-pyrrolidino-valeryl)-6H-pyrido[2,3-b][1,4]-benzodiazepin-6-one 4.5 gm of 11-(5-chlorovaleryl)-5,11-dihydro-6H-pyrido [2,3-b][1,4]-benzodiazepin-6-one and 10 ml of pyrrolidine were refluxed in 100 ml of ethanol for 12 hours. The alcohol was then distilled off, the residue was dissolved in chloroform/water, the organic phase was evaporated in vacuo to dryness, and the residue was recrystallized from ethyl acetate.
M.p.: 157°–159° C.
Yield: 45% of theory.

EXAMPLE 13

11-{[(1-Benzyl-2-pyrrolidinyl)-methylamino]acetyl}-5,11-dihydro-5-methyl-6H-pyrido[2,3-b][1,4]benzodiazepin-6-one 14.3 gm of 11-chloroacetyl-5,11-dihydro-5-methyl-6H-pyrido [2,3-b][1,4]benzodiazepin-6-one, 5.3 gm of sodium carbonate and 11.4 gm of 2-aminomethyl-1-benzyl-pyrrolidine were refluxed for 2 hours in 300 ml of absolute dioxane. The mixture was filtered while still hot, the dioxane was evaporated, and the residue was purified on a silica gel column. The eluate was evaporated, and the residue was recrystallized twice from ethyl acetate.
M.p.: 123°–124° C.
Yield: 47% (of theory).

The column-chromatographic purifications of the raw products were carried out in the above examples on a silica gel column, using a mixture of chloroform, methanol, cyclohexane and concentrated ammonia in a proportion of 68:15:15:2 as the solvent and eluant.

The compounds of the formula I listed in the following table were also prepared:

| Ex. | $R_1$ | $R_2$ | A | M.p. (recryst. from) | Yield % | Prepared acc. to Ex. |
|---|---|---|---|---|---|---|
| 14 | $-N(CH_3)_2$ | H | $-(CH_2)_3-$ | Hydrochloride: M.p.: 207°–209° C. (decomp.) (Acetonitrile) | 48 | 8 |
| 15 | $-N(C_2H_5)_2$ | $CH_3$ | $-CH_2-CH_2-$ | Hydrochloride: M.p.: 230°–232° C. (Ethanol/Isopropanol) | 39 | 2 |
| 16 | $-N(C_2H_5)_2$ | H | $-(CH_2)_3-$ | Hydrochloride: M.p.: 209°–211° C. (Acetonitrile) | 44 | 8 |
| 17 | $-N(CH_2-CH(CH_3)_2)_2$ | $CH_3$ | $-(CH_2)_3-$ | M.p.: 145°–147° C. (cyclohexane) | 30 | 3 |
| 18 | $-NH-C(CH_3)_3$ | H | $-CH_2-$ | M.p.: 198°–200° C. (ethyl acetate/chloroform) | 37 | 6 |
| 19 | $-N(CH_3)$(cyclohexyl-H) | H | $-CH_2-$ | M.p.: 213°–215° C. (Isopropanol) | 63 | 2 |
| 20 | $-NH-CH_2-$phenyl | H | $-CH_2-$ | M.p.: 170°–174° C. (Acetonitrile) | 35 | 6 |
| 21 | $-NH-CH_2-$(3,4,5-trimethoxyphenyl) | H | $-CH_2-$ | M.p.: 198°–200° C. (decomp.) (n-Propanol) | 36 | 6 |

-continued

| Ex. | R$_1$ | R$_2$ | A | M.p. (recryst. from) | Yield % | Prepared acc. to Ex. |
|---|---|---|---|---|---|---|
| 22 | −NH−CH$_2$−[pyrrolidine, N−C$_2$H$_5$] | H | −CH$_2$− | M.p.: 173°–174° C. (Isopropanol) | 79 | 6 |
| 23 | −NH−CH$_2$−[pyrrolidine, N−C$_2$H$_5$] | H | −CH$_2$−CH$_2$− | M.p.: 140°–143° C. (ethyl acetate) | 48 | 6 |
| 24 | −N[pyrrolidine] | H | −CH$_2$−CH$_2$− | M.p.: 204°–207° C. (decomp.) (Acetonitrile) | 83 | 4 |
| 25 | −N[pyrrolidine] | CH$_3$ | −CH$_2$−CH$_2$− | M.p.: 155°–156° C. (Xylene) | 88 | 4 |
| 26 | −N[pyrrolidine] | CH$_3$ | −(CH$_2$)$_3$− | M.p.: 122°–123° C. (Butylacetate) | 21 | 3 |
| 27 | −N[piperidine] | CH$_3$ | −CH$_2$−CH$_2$ | M.p.: 160°–162° C. (Xylene) | 53 | 4 |
| 28 | −N[piperidine] | H | −(CH$_2$)$_3$− | M.p.: 157°–158° C. (Acetonitrile) | 33 | 3 |
| 29 | −N[piperidine] | CH$_3$ | −(CH$_2$)$_3$− | M.p.: 124°–125° C. (Isopropanol) | 26 | 3 |
| 30 | −N[piperidine, CH$_3$] | CH$_3$ | −CH$_2$−CH$_2$− | M.p.: 104°–106° C. (Isopropanol) Hydrochloride: M.p.: 260°–262° C. (Methanol/ethanol) | 90 | 4 |
| 31 | −N[piperidine, CH$_3$] | H | −(CH$_2$)$_3$− | M.p.: 174°–175° C. (Acetonitrile) | 29 | 8 |
| 32 | −N[piperidine, C$_2$H$_5$] | H | −CH$_2$−CH$_2$− | M.p.: 185°–187° C. (decomp.) (Acetonitrile) | 78 | 4 |

-continued

| Ex. | R₁ | R₂ | A | M.p. (recryst. from) | Yield % | Prepared acc. to Ex. |
|---|---|---|---|---|---|---|
| 33 | 2-ethylpiperidin-1-yl | CH₃ | —CH₂—CH₂— | M.p.: 115°–116° C. (Cyclohexane) | 53 | 4 |
| 34 | 3-hydroxypiperidin-1-yl | H | —CH₂— | M.p.: 218°–219° C. (Ethanol/Ether) | 63 | 2 |
| 35 | 4-hydroxypiperidin-1-yl | H | —CH₂— | M.p.: 247°–248° C. (Ethanol/Ether) | 54 | 2 |
| 36 | 4-benzylpiperidin-1-yl | H | —CH₂— | M.p.: 228°–230° C. (Ethanol) | 60 | 6 |
| 37 | 3-azaspiro[5.5]undecan-3-yl | H | —CH₂— | M.p.: 216°–218° C. (Acetonitrile) | 59 | 2 |
| 38 | 4-oxopiperidin-1-yl | H | —CH₂— | M.p.: 223°–225° C. (decomp.) (Ethanol) | 43 | 6 |
| 39 | 4-oxopiperidin-1-yl | CH₃ | —CH₂— | M.p.: 177°–178° C. (Isopropanol) | 39 | 6 |
| 40 | 4-oxopiperidin-1-yl | H | —CH₂—CH₂— | M.p.: 210°–212° C. (decomp.) (Ethanol) | 24 | 6 |
| 41 | 1,4-dioxa-8-azaspiro[4.5]decan-8-yl | H | —CH₂— | M.p.: 219°–221° C. (Isopropanol) | 72 | 6 |
| 42 | 1,4-dioxa-8-azaspiro[4.5]decan-8-yl | CH₃ | —CH₂— | M.p.: 191°–192° C. (Ethanol) | 83 | 6 |
| 43 | 1,4-dioxa-8-azaspiro[4.5]decan-8-yl | H | —CH₂—CH₂— | M.p.: 228°–230° C. (Ethanol) | 18 | 2 |
| 44 | 1,4-dioxa-8-azaspiro[4.5]decan-8-yl | H | —(CH₂)₃— | M.p.: 138°–140° C. (ethyl acetate) | 27 | 7 |

-continued

| Ex. | R₁ | R₂ | A | M.p. (recryst. from) | Yield % | Prepared acc. to Ex. |
|---|---|---|---|---|---|---|
| 45 | -N⟨tetrahydropyridine⟩ | H | —CH₂— | M.p.: 217°–219° C. (Isopropanol) | 58 | 6 |
| 46 | -N⟨morpholine⟩O | H | —CH₂—CH₂— | M.p.: 208°–210° C. (decomp.) (Acetonitrile) | 85 | 4 |
| 47 | -N⟨morpholine⟩O | CH₃ | —CH₂—CH₂— | M.p.: 200°–202° C. (Xylene) | 55 | 4 |
| 48 | -N⟨2,6-dimethylmorpholine⟩ | H | —CH₂— | M.p.: 262°–264° C. (Isopropanol) | 51 | 4 |
| 49 | -N⟨thiomorpholine⟩S | H | —CH₂— | M.p.: 246°–248° C. (n-Propanol) | 62 | 6 |
| 50 | -N⟨thiomorpholine-S-oxide⟩S=O | H | —CH₂— | M.p.: 245°–246° C. (n-Propanol) | 59 | 6 |
| 51 | -N⟨tetrahydroisoquinoline⟩ | H | —CH₂— | M.p.: 210°–211° C. (Isopropanol) | 72 | 2 |
| 52 | -N⟨4-methylpiperazine⟩N—CH₃ | H | —CH₂— | M.p.: 214°–216° C. (Isopropanol) | 45 | 6 |
| 53 | -N⟨N-methyl-diazabicyclo⟩N—CH₃ | H | —CH₂— | M.p.: 237°–240° C. (decomp.) (Isopropanol) | 57 | 6 |
| 54 | (bicyclic diamine structure, two tautomers) | H | —CH₂— | M.p.: 237°–239° C. (Ethanol) | 46 | 6 |

| Ex. | R₁ | R₂ | A | M.p. (recryst. from) | Yield % | Prepared acc. to Ex. |
|---|---|---|---|---|---|---|
| 55 |  | CH₃ | —CH₂—CH₂— | Hydrochloride M.p.: 220°–221° C. (Acetonitrile) | 47 | 3 |
| 56 | 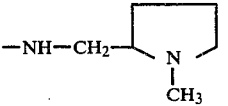 | H | —CH₂— | 168°–170° C. (ethyl acetate) | 49 | 6 |
| 57 | 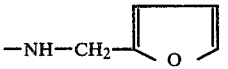 | H | —CH₂— | 181°–183° C. (ethanol) | 50 | 1 |
| 58 | 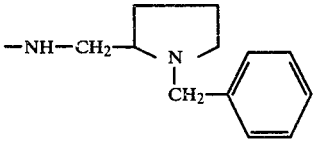 | H | —CH₂— | 179°–180° C. (ethanol) | 30 | 13 |
| 59 | 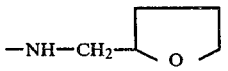 | H | —CH₂— | 169°–171° C. (acetonitrile) | 51 | 5 |
| 60 | 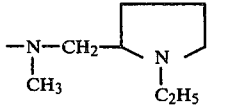 | H | —CH₂— | 143°–145° C. (cyclohexane/ethyl acetate) | 43 | 13 |
| 61 | 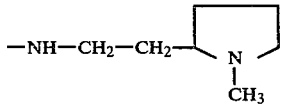 | H | —CH₂— | 154°–156° C. (butyl acetate) | 31 | 13 |
| 62 | 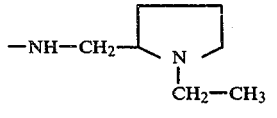 | CH₃ | —CH₂—CH₂— | 84°–86° C. (cyclohexane/ethyl acetate | 49 | 13 |
| 63 | 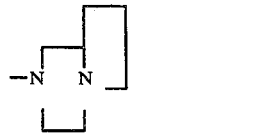 | H | —CH₂— | 219°–221° C. (isopropanol) | 63 | 1 |
| 64 | 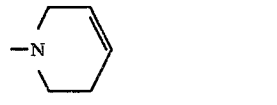 | CH₃ | —CH₂— | 162°–163° C. (isopropanol) | 81 | 1 |
| 65 | 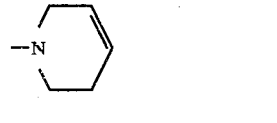 | H | —CH₂—CH₂— | 207°–209° C. (ethanol) | 65 | 1 |
| 66 | 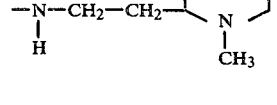 | CH₃ | —CH₂— | 141°–144° C. (ethyl acetate) | 32 | 1 |

-continued

| Ex. | R₁ | R₂ | A | M.p. (recryst. from) | Yield % | Prepared acc. to Ex. |
|---|---|---|---|---|---|---|
| 67 | −NH−CH₂−(N-methylpyrrolidin-2-yl) | CH₃ | −CH₂− | 179°–181° C. (isopropanol) | 54 | 1 |
| 68 | −NH−CH₂−(N-ethylpyrrolidin-2-yl) | C₂H₅ | −CH₂− | 119°–120° C. (acetontrile) | 46 | 1 |
| 69 | −NH−CH₂−(N-propylpyrrolidin-2-yl) | CH₃ | −CH₂− | 147°–148° C. (ethyl acetate) | 52 | 1 |
| 70 | −NH−CH₂−(N-allylpyrrolidin-2-yl) | CH₃ | −CH₂− | 123°–125° C. (ethyl acetate/cyclohexane) | 45 | 6 |
| 71 | −NH−CH₂−(N-butylpyrrolidin-2-yl) | CH₃ | −CH₂− | 64°–67° C. (ethyl acetate/cyclohexane) | 34 | 6 |
| 72 | −NH−CH₂−(N-ethylpyrrolidin-2-yl) | CH₃ | −(CH₂)₅− | Hydrobromide 186°–188° C. (isopropanol/ethanol) | 50 | 5 |
| 73 | −N(piperidin-1-yl) | H | −(CH₂)₅− | 140°–142° C. (ethyl acetate) | 58 | 5 |
| 74 | −NH−CH₂−(N-propylpyrrolidin-2-yl) | H | −CH₂− | 150°–152° C. (acetontrile) | 41 | 6 |
| 75 | −NH−CH₂−(N-allylpyrrolidin-2-yl) | H | −CH₂− | 126°–128° C. (ethyl acetate/cyclohexane) | 35 | 6 |
| 76 | −NH−CH₂−(N-ethylpyrrolidin-2-yl) | CH₃ | −CH₂− | 97°–100° C. (diethyl ether) | 41 | 6 |
| 77 | −NH−CH₂−(N-butylpyrrolidin-2-yl) | H | −CH₂− | 114°–116° C. (butyl acetate) | 31 | 6 |

-continued

| Ex. | R₁ | | R₂ | A | M.p. (recryst. from) | Yield % | Prepared acc. to Ex. |
|---|---|---|---|---|---|---|---|
| 78 | —NH—CH₂—[piperidine ring, N-substituted with CH₂—CH=CH₂] | | CH₃ | —CH₂— | 78°–81° C. (diethyl ether) | 27 | 6 |
| 79 | —NH—CH₂—[piperidine ring, N-substituted with C₂H₅] | | H | —CH₂— | 86°–88° C. (diethyl ether) | 32 | 6 |

The compounds of the present invention, that is, those embraced by formula I above and their non-toxic, pharmacologically acceptable addition salts, have useful pharmacodynamic properties. More particularly, they exhibit anti-ulcerogenic and secretion inhibiting activities in warm-blooded animals, such as mice and rats. Thus, the compounds of the present invention are useful for the treatment of gastric and duodenal ulcers, gastritis and similar diseases of the stomach and intestines.

The above pharmacological properties of the compounds of this invention were ascertained by the methods described below, and the tables show the results of these tests for a few representative species, where 11-{[(1-ethyl-2-pyrrolidinyl)methylamino]acetyl}-5,11-dihydro-5-methyl-6H-pyrido[2,3-b][1,4]benzodiazepine-6-one=A, 5,11-dihydro-11-[(4-methoxypiperidino)acetyl]-6H-pyrido-[2,3-b][1,4]benzodiazepine-6-one=B, 5,11-dihydro-11-[3-(2-methylpiperidino)propionyl]-6H-pyrido-[2,3-b][1,4]benzodiazepine-6-one=C, 5,11-dihydro-11-[(3-piperidinopropionyl)]-6H-pyrido[2,3-b]-[1,4]benzodiazepine-6-one=D, and 5,11-dihydro-11-(4-pyrrolidino-butyryl)-6H-pyrido[2,3-b]-[1,4]benzodiazepine-6-one=E.

The compounds were examined with regard to their inhibiting effect on the formation of stress ulcers in rats and their spasmolytic effect, related to atropine, with consideration of their acute toxicity.

The inhibiting effect on the formation of stress ulcers in rats was determined according to the method of K. Takagi and S. Okabe, Jap.Journ.Pharmac. 18, pp. 9 to 18 (1968). Fed female rats with a body weight between 220 and 260 gm were individually put into small wire cages and were subsequently kept vertically submerged in a water bath which was kept constant at a temperature of 23° C. for 16 hours, so that only the heads and the breastbones of the animals were above the water surface. The test compounds were administered perorally 5 to 10 minutes before. With each substance five animals were treated. 1 ml of a 0.9% physiological sodium chloride solution or 1 ml of a 1% tylose solution was administered to the control animals in the same way. After 18 hours the animals were killed by an overdose of ethyl chloride, the stomachs were excised, cut along the big curvature and spread on a cork plate. The evaluation was carried out according to the methods of Marazzi-Uberti and Turba, Med. Exp. 4, pp. 284 to 292 (1961), and Takagi and Okabe (supra).

The spasmolytic effect was determined in vitro on the guinea pig colon, using the experimental arrangement according to R. Magnus, Pflügers Archiv, 102, pp. 123 (1904). Acetylcholine was taken to induce spasms, the substance for comparison was atropinesulfate. The spasticum was administered one minute before the administration of the spasmolytic substance, and the spasmolytic was allowed to take effect for 1 minute. In rats it was also observed that the atropine-like side-effects, such as inhibition of salivary secretion, were completely missing or remarkably decreased when the substances A to E were administered. The acute toxicity was determined after peroral administration of the test substance to fasted white mice with a body weight of 18 to 20 gm. The observation period was 14 days. For each dosage a group of six mice was used.

| | Ulcer-inhibition in % (rat) after peroral administr. of | | | Spasmolysis (acetylcholine) with regard to Atropin = 1 | LD₅₀ peroral mg/kg mouse |
|---|---|---|---|---|---|
| Compound | 50 | 25 | 12.5 | | |
| | mg/kg | | | | |
| A | 95 | 90 | 90 | 1/250 | ~1500* |
| B | 89 | 79 | 53 | 1/125 | >1000** |
| C | 95 | 84 | 79 | 1/50 | >1000*** |
| D | 84 | 69 | 58 | 1/125 | ~2000**** |
| E | 79 | 58 | 18 | 1/190 | >1500***** |

*at 1500 mg/kg 2 out of 4 animals died
**at 1000 mg/kg 2 out of 5 animals died
***at 1000 mg/kg 1 out of 5 animals died
****at 2000 mg/kg 3 out of 5 animals died
*****at 1500 mg/kg 1 out of 6 animals died The spasmolytic effect of the compounds A to E in comparison to that of atropine sulfate is remarkably weaker and therefore also the atropine-like side-effects.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective oral dosage unit of the compounds according to the present invention is from 0.083 to 0.83 mgm/kg body weight, preferably 0.16 to 0.5 mgm/kg body weight. The daily dose rate is 0.3 to 1.7 mgm/kg, preferably 0.5 to 1.5 mgm/kg.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 80

Tablets

The tablet composition is compounded from the following ingredients:

| | |
|---|---:|
| 11 {[(1-Ethyl-2-pyrrolidinyl)methyl-amino]acetyl}-5,11-dihydro-5-methyl-6H-pyrido[2,3-b][1,4]benzodiazepin-6-one | 10.0 parts |
| Lactose | 148.0 parts |
| Potato starch | 60.0 parts |
| Magnesium Stearate | 2.0 parts |
| Total | 220.00 parts |

Preparation:

An aqueous 10% slurry is prepared by heating a portion of the potato starch. The active ingredient, the lactose and the remaining potato starch admixed with each other, and the mixture is granulated by passing it, together with the above slurry, through a 1.5 mm mesh screen. The granulate is dried at 45° C., again passed through the screen, admixed with the magnesium stearate, and the composition is compressed into 220 mgm-tablets. Each tablet is an oral dosage unit composition containing 10 mgm of the active ingredient.

EXAMPLE 81

Coated Pills 220 mgm-pill cores are prepared from the same ingredients and in the same manner as in Example 80. The pill cores are then coated with a thin shell consisting essentially of talcum and sugar, and finally polished with beeswax in conventional manner.

EXAMPLE 82

Hypodermic Solution

The solution is compounded from the following ingredients:

| | |
|---|---:|
| 11-{[(1-Ethyl-2-pyrrolidinyl)methyl-amino]acetyl}-5,11-dihydro-5-methyl-6H-pyrido[2,3-b][1,4]benzodiazepine-6-one-dihydrochloride | 2.0 parts |
| Sodium chloride | 8.0 parts |
| Distilled water q.s.ad | 1000.0 parts by vol. |

Preparation:

The active ingredient and the sodium chloride are dissolved in a sufficient amount of distilled water, and the solution is diluted with additional distilled water to the indicated volume. The solution is then filtered until free from suspended particles and subsequently filled into 1 cc-ampules, which are finally sterilized at 120° C. for 20 minutes and sealed. The contents of each ample are an injectable solution containing 2 mgm of the active ingredient.

EXAMPLE 83

Suppositories

The suppository composition is compounded from the following ingredients:

| | |
|---|---:|
| 11-{[(1-Ethyl-2-pyrrolidinyl) methyl-amino]acetyl}-5,11-dihydro-5-methyl-6H-pyrido[2,3-b][1,4]benzodiazepin-6-one | 15.0 parts |
| Suppository base (e.g. cocoa butter) | 1685.0 parts |
| Total | 1700.0 parts |

Preparation:

The suppository base is melted and cooled to 40° C., the milled active ingredient is homogeneously dispersed therein, the mixture is cooled to 37° C., and 1700 mgm portions thereof are poured into cooled suppository molds and allowed to harden therein. Each suppository is a rectal dosage unit composition containing 15 mgm of the active ingredient.

EXAMPLE 84

Drop Solution

The solution is compounded from the following ingredients:

| | |
|---|---:|
| 11-{[1-Ethyl-2-pyrrolidinyl)methyl-amino]acetyl}-5,11-dihydro-5-methyl-6H-pyrido[2,3-b][1,4]benzodiazepin-6-one-dihydrochloride | 1.0 parts |
| Methyl p-hydroxy-benzoate | 0.035 parts |
| Propyl p-hydroxy-benzoate | 0.015 parts |
| Oil of anise | 0.05 parts |
| Menthol | 0.06 parts |
| Ethanol, pure | 10.0 parts |
| Sodium cyclamate | 1.0 parts |
| Gylcerin | 15.0 parts |
| Distilled water q.s. ad | 100.0 parts by vol. |

Preparation:

The active ingredient and the sodium cyclamate are dissolved in about 70 parts by volume of water, and the glycerin is added to the solution. The p-hydroxy-benzoates, the oil of anise and the menthol are dissolved in the ethanol, and the solution is added to the aqueous solution while stirring. The mixed solution is diluted with distilled water to the indicated volume, and is then filtered until free from suspended particles. 1 ml (20 drops) of the filtrate is an oral dosage unit composition containing 10 mgm of the active ingredient.

Any one of the other pyridobenzodiazepinones embraced by formula I or a non-toxic, pharmacologically acceptable acid addition salt thereof may be substituted for the particular pyridobenzodiazepinone compound in Examples 80 through 84. Likewise, the amount of ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

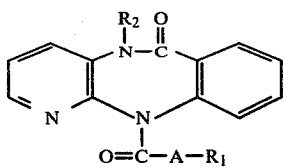

wherein
A is methylene or ethylene,
$R_1$ is (1-ethyl-pyrrolidin-2-yl)-methyl-amino, (1-methyl-pyrrolidin-2-yl)-methyl-amino, (1-methyl-pyrrolidin-2-yl)-ethyl-amino, (1-n-propyl-pyrrolidin-2-yl)-methyl-amino or (1-allyl-pyrrolidin-2yl)-methyl-amino; and
$R_2$ is hydrogen or methyl;
or a non-toxic, pharmacologically acceptable acid addition salt thereof.

2. A compound of claim 1, which is 11-{[2-(1-methyl-pyrrolidin-2-yl)-ethyl-amino]-acetyl}-5,11-dihydro-6H-pyrido[2,3-b][1,4]benzodiazepin-6-one or a non-toxic, pharmacologically acceptable acid addition salt thereof.

3. A compound of claim 1, which is 5,11-dihydro-11-{[(1-methyl-pyrrolidin-2-yl)-methyl-amino]-acetyl}-6H-pyrido[2,3-b][1,4]benzodiazepin-6-one or a non-toxic, pharmacologically acceptable acid addition salt thereof.

4. An anti-ulcerogenic or secretion-inhibiting pharmaceutical dosage unit composition consisting essentially of an inert pharmaceutical carrier and an effective antiulcerogenic or secretion-inhibiting amount of a compound of claim 1.

5. The method of treating gastro-intestinal ulcers or inhibiting gastro-intestinal secretion in a warm-blooded animal, which comprises perorally, parenterally or rectally administering to said animal an effective anti-ulcerogenic or secretion-inhibiting amount of a compound of claim 1.

* * * * *